United States Patent [19]

Volgushev

[11] Patent Number: 5,472,404
[45] Date of Patent: Dec. 5, 1995

[54] METHOD FOR SURGICAL CORRECTION OF VASCULAR OCCLUSIONS

[76] Inventor: Valentin E. Volgushev, Dolgoprudny, ulitsa Oktyabrskaya, 22, korpus 1, kv. 103, Moskovskaya oblast, Russian Federation

[21] Appl. No.: 391,367

[22] Filed: Feb. 21, 1995

[51] Int. Cl.$^6$ .................................................. A61F 2/04
[52] U.S. Cl. .................................. 600/36; 623/1; 623/11
[58] Field of Search ....................... 600/36, 152, 153; 623/1, 2, 11, 16

[56] References Cited

U.S. PATENT DOCUMENTS

| | | | |
|---|---|---|---|
| 3,625,198 | 12/1971 | Sparks | 600/36 |
| 3,707,958 | 1/1973 | Sparks | 600/36 |
| 3,710,777 | 1/1973 | Sparks | 128/1 R |
| 3,866,609 | 2/1975 | Sparks | 600/36 |

FOREIGN PATENT DOCUMENTS 1331491  8/1987  U.S.S.R. .

OTHER PUBLICATIONS

Pashenko, Z. A., et al., "Plastic Surgery of Aorta . . . " Surgery, No. 2, Meditsina Publishers, Moscow (1978), pp. 114–117.

Pashenko, Z. A., et al. "New Modification of Semibiological . . . " Zdravookhraneniye Belorussii, No. 6, (1974), Minsk, pp. 23–25.

Concise Medical Encyclopedia, vol. 3, Moscow, 1966, pp. 814–815.

Concise Medical Encyclopedia, vol. 4, Moscow, 1966, p. 800.

Concise Medical Encyclopedia, vol. 5, Moscow, 1967, pp. 946–947.

*Primary Examiner*—Randall L. Green
*Assistant Examiner*—Rob Clarke
*Attorney, Agent, or Firm*—Ladas & Parry

[57] ABSTRACT

A method for surgical correction of vascular occlusions involving replacement of the affected portion of the vessel with a vascular autotransplant grown in the patient's tissues around the modelled preform from a magnetic alloy which speeds up killing, reduces the risk of thromboses, infection and rejection and forestalls the development of the destructive processes in the wall of the autotransplant.

2 Claims, 3 Drawing Sheets

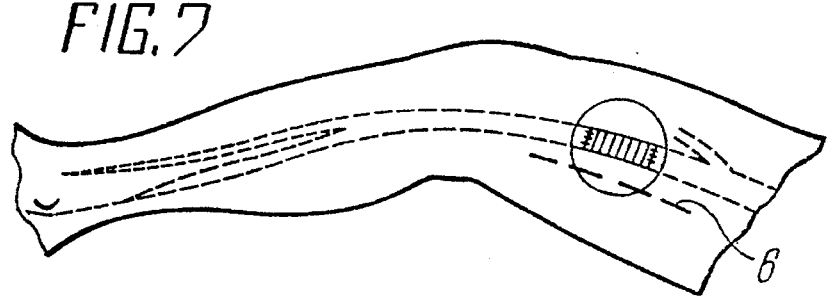
FIG. 7
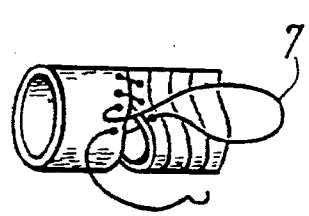
FIG. 8
FIG. 7A
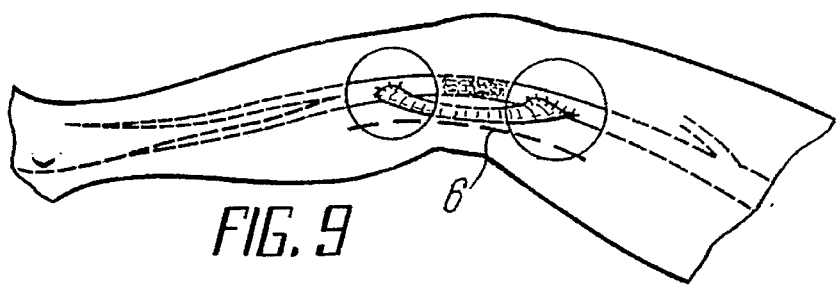
FIG. 9
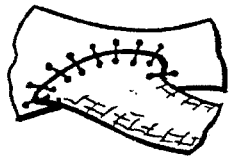
FIG 9A
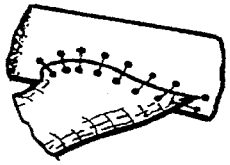
FIG. 9B
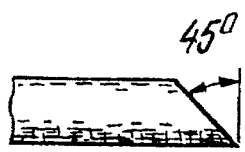
FIG. 10
FIG. 11
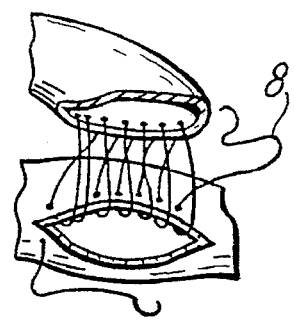
FIG. 12

METHOD FOR SURGICAL CORRECTION OF VASCULAR OCCLUSIONS

FIELD OF ART

The present invention relates to medicine and, more specifically, to vascular and cardiac surgery.

PRIOR ART

Known in the prior art is a method for plastic surgery of vessels involving preliminary embedding of an artificial vascular prosthesis on a flexible plastic mandrel into the muscular tissues of the patient close to the damaged vessel and suturing the operative wound. Then, after the formation of a biological envelope in the course of 1–1.5 months the flexible mandrel is pulled out of the prosthesis through the incision, the transplant formed around the artificial vascular prosthesis is shifted in place instead of the ablated vessel segment without interfering with the sources of innervation and blood supply of its biological component, and the ends of the remaining vessel are sutured to the transplant by applying anastomoses of the "end-to-side" or "end-to-end" type (Inventor's Certificate USSR No. 1334191, cl. A61B17/00, 1979).

The disadvantages of this method include a high risk of thrombosis, infection and rejection of the transplant caused by the presence of a foreign body—prosthesis frame—in in the vascular bed.

DISCLOSURE OF THE INVENTION

The main object of the invention resides in promoting the efficiency of the method by making a high-quality autotransplant, reducing the thrombosis hazard, infection and rejection, as well as forestalling the development of destructive processes in the transplant wall.

The above problem is solved in a method for surgical correction of vascular occlusions involving preliminary formation of a vascular transplant in the patient's tissues and moving it in place of the ablated segment of the affected vessel wherein, according to the invention, after identifying the portion of the damaged vessel the next steps comprise modelling and making a cylindrical mandrel (solid cylinder) from an alloy possessing magnetic properties, e.g. a cobalt-samarium alloy (63% cobalt, 37% samarium); the main characteristics of the magnetically-hard baked material: maximum product of residual induction (B) by coercive force (H) at least 110 kJ/cu.m (BH/max); coercive force (H), not under 540 kA/m and residual induction (Br), not under 0.77 T or from barium ferrite with the diameter of the preform corresponding to that of the affected vessel.

The autotransplant is prepared by embedding a modelled preform with a straight packer through a point-like incision of skin into the subcutaneous fat of the front abdominal wall or into the subclavian region of the patient for 21–29 days until a three-layer capsule grows around the preform. By the end of the 1st week after embedding the preform having the properties of a permanent magnet into the subcutaneous fat, the layers of the biocapsule start forming beginning from the outer layer surrounded by a layer of granulation tissue. By the end of the 2nd week all the three yet incompletely formed layers become discernible and the young connective tissue with a delicate network of blood capillaries growing inward from outside can be clearly identified. By the end of the 3rd week all layers can be clearly observed: endothelium-like lining, argyrophil and elastic fibers around a thin hyoline layer in the form of a membrane, and connective tissue with a plurality of elastic and collagenic fibers containing a developed network of capillaries, large arteries and veins with all clearly differentiated layers of their walls. However, the 2nd and 3rd layers may have individual thinned-out "islands". By the middle and end of the 4th week all the layers are well formed and homogeneous, including the endothelium-like lining uniformly disposed along the internal wall of the biocapsule. Thus, the biocapsule is fully formed within 21–29 days. Meanwhile, the patient lives normally at home and makes all the requisite analyses for hospitalization and operative treatment. 21–29 days after embedding the preform into the subcutaneous fat of the patient, access is opened to the affected artery. Simultaneously a linear incision is made to dissect the skin in the projection of the embedded preform, said preform overgrown with the capsule is exposed and used to prepare an autotransplant for replacing the affected portion of the vessel—either by cutting off both ends of the biocapsule with a scalpel at an angle of 90 deg to its length and removing the preform when using it as an autoprosthesis and autobypass or by cutting out a "patch" of an appropriate shape and size from its side wall.

In the course of the 1st month after the operation the vessels of the sound portion of the patient's resected artery grow into the connective tissue of the autotransplant forming an extension of the adventitia and media of the sound vascular wall. By the end of the 1st month the endothelium is completely formed in place of the endothelium-like lining. Said endothelium is formed not only from the endothelium of the recipient's sound vascular wall but also from numerous large arteries and veins and their internal linings as well as from the vasa vasorium developed in the wall of the autotransplant. This type of regeneration is referred to as reparative (reconstructive) and consists in replacing the defect with a tissue identical to that of the vascular wall. The transplant grafting rate is increased due to the absence of the foreign artificial prosthesis frame.

The magnetic properties of the preform made, for example, of an alloy featuring the properties of a permanent magnet contribute to the speedier development of the capsule around the preform.

Being a liquid tissue, blood functions at the same time as an electrolyte. The basic blood cation is iron concentrated in the hemoglobin of erythrocytes while plasma contains the so-called nonhemoglobin iron. Apart from iron, blood contains other metals such as magnesium, zinc, copper. Out of anions, chlorine, iodine and bromine should be mentioned (Concise Medical Encyclopedia, 1966, Vol. 4, pp 946–947).

According to the theory of germinal layers that came to be termed the basic law of development, the entire circulatory system, all types of internal tissues (adventitia with all its components, muscular tissue, endothelium of vessels) develops from mesoderm containing mesenchyme (Concise Medical Encyclopedia, 1967, Vol. 5, p. 799).

The cells of the adipose tissue and subcutaneous fat are, among others, also a derivative of mesenchyme. The intercellular space is occupied by the collagenic, reticular and elastic fibers, a developed network of blood capillaries, and nerve fibers. Experiments proved the ability of this tissue acted upon by external factors to regenerate into hemopoietic tissue, into yellow bone marrow and into tissues of the mesoderm origin (Concise Medical Encyclopedia, 1966, Vol. 3, pp 814–815).

The modern experimental embryology and gene engineering have demonstrated that the cells of one tissue belonging to a single germinal layer can, under changed conditions, produce the derivatives of the cells of another tissue related to the same germinal layer. The same is confirmed by many factors in the sphere of tissue regeneration of adult animals and man in a permanent magnetic field. Owing to close kinship of the subcutaneous fat with the tissues of the vessel wall, its abundant blood supply through the developed network of small blood capillaries and easy access due to its shallow location, the subcutaneous fat was selected as the place for implanting a permanent magnet.

It is a well-established fact that the permanent magnetic field favors the changes in the permeability of cell membranes due to severance by the permanent magnetic field of the equilibrium bonds between electrolyte (blood and other body liquids) and body ions which results in magnetic dissociation and ionization of molecules. This improves the rheological characteristics of blood, changes the progress of bioenergetic processes and trophicity of tissues. All this stimulates regeneration under the new conditions.

The development of a more differentiated three-layer biocapsule in the subcutaneous fat is achieved by the positive influence of the permanent magnetic field upon the regenerative capacities of the tissues formed from mesoderm. In its turn the analogous three-layer structure of the biocapsule wall and of the walls of the resected vessel draws closer their histomorphological structure and reduces the thrombosis hazard; a high histomorphological homogeneity brings closer their physicomechanical properties and reduces the danger of destructive processes; the absence of a foreign prosthesis frame and, consequently, of its contact with blood in the vascular channel reduces the thrombosis hazard, infection, rejection and destruction of the autotransplant. Only a preform made from a material with magnetic properties permits producing a three-layer biological capsule around the preform. Said capsule is suitable for use as a vascular transplant because the effect of the permanent magnetic field and molecular magnetic dissociation it originates, one of the substrates of said dissociation consisting of blood microelements, increases the permeability of cellular membranes through breaks in the equilibrium bonds between electrolyte (blood and other fluid bodies) and body ions, thus improving the rheological properties of blood. This changes the nature of bioenergetic processes, trophicity of tissues, stimulates regeneration under new conditions. There are known cases of encapsulation of foreign bodies in the organism, e.g. shell splinters in the human body.

However, if the foreign body possesses no magnetic properties, its encapsulation takes considerably more time. The use of such a capsule for a vascular prosthesis is impossible since its structure consists predominantly of a coarse connective tissue and because of practically instant thrombosis of this vascular prosthesis. The use of preforms from nonmagnetic materials even within periods up to 6 months fails to produce a biocapsule around the preform which could be used independently in the capacity of a vascular autotransplant. On the contrary, making preforms form materials featuring the properties of a permanent magnet (cobalt-samarium or barium ferrite) ensures the development of a biocapsule at a shorter date, i.e. in 21–29 days and makes it suitable for use as a vascular autotransplant.

BRIEF DESCRIPTION OF THE DRAWINGS

FIG. 7—using autotransplant as autoprosthesis in femoral prosthetics;

FIG. 8—"end-to-end" anastomosis in femoral prosthetics, diagrammatic;

FIG. 9—autotransplant used as an autobypass in femoral-popliteal shunting;

FIG. 10—preparation of the distal end of autotransplant, diagrammatic;

FIG. 11—preparation of the proximal end of the autotransplant, diagrammatic;

FIG. 12—"end-to-side" anastomosis in femoral-popliteal shunting;

DETAILED DESCRIPTION OF THE INVENTION

The method is realized as follows.

After making a diagnosis and indications of operative treatment, the section of the affected artery is identified by aorto-arteriography (or coronarygraphy).

Figure 1:
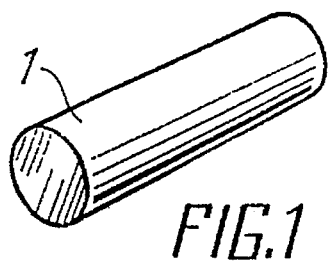
FIG. 1 illustrates a preform made from a magnetic alloy.
Figure 2:
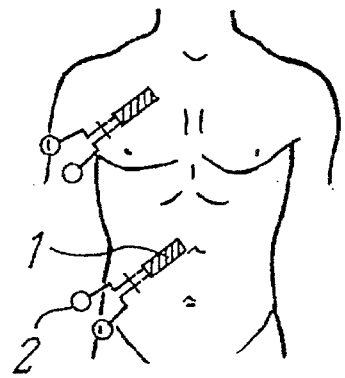
FIG. 2 is a diagram showing the embedding of a preform made from a magnetic alloy.
Figure 3:
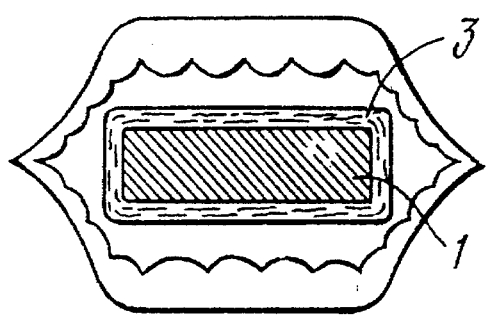
FIG. 3 shows dissection of skin in the projection of the preform.

On the basis of the obtained results a cylindrical solid preform 1 (FIG. 1) without an inner cavity is modelled from a magnetic metal alloy, for example cobalt-samarium alloy or barium ferrite, of a diameter corresponding to the diameter and anatomy of the damaged artery of the patient. The autotransplant is prepared by inserting the prepared preform with a packer 2 through a point-like incision of the skin into the subcutaneous fat on the front abdominal wall or subclavian region of the patient for 21–29 days (FIG. 2) until a three-layer capsule 3 is formed around the preform. Then the skin is dissected along the projection of the preform (FIG. 3).

Depending on the nature of the disease, the autobiocapsule can be used either as an autoprosthesis, autobypass or the autopatch of vessels.

Let us consider the use of the autotransplant in the capacity of an autoprosthesis on the example of prosthetics of the femoral artery.

After making the diagnosis, the patient is administered to aorta-arteriography to determine the indications for operation and modelling the preform 1 (FIG. 1) made of a magnetic metal alloy. The length and diameter of the preform shall correspond to the anatomy of the affected fragment of the patient's femoral artery. Under local anesthesia with a 0.25-% solution of novocaine the preform 1 is inserted with the packer 2 (FIG. 2) through the point-like skin section and the formed tunnel into the subcutaneous fat of the patient, on his front abdominal wall. In the course of 21–29 days the patient lives his normal life then hospitalized before operation. On the day of the operation, the patient is given anesthesia, simultaneously obtaining access to the affected portion of the femoral artery, then the skin is dissected in the projection of the preform 1 at the point of its location (FIG. 3), the preform 1 with the capsule 3 formed around it is exposed from the surrounding tissues, the edges of the capsule are cut off with a scalpel 4, stepping back up to 1 cm from both ends (FIG. 4), the preform (FIG. 5) is pulled out of it and the resulting autotransplant 5 (FIG. 6) is used as autoprosthesis of the femoral artery. Then the prosthetics of the femoral artery is conducted according to the standard methods (FIG. 7). The exposed artery is clamped with artery forceps proximally to and distally from the failed fragment which is resected within the limits of the intact portion. According to the length of the resected vessel, each end of the autotransplant is ablated at 90 deg so as to match the length of the autotransplant with that of the resected vessel. For this purpose the length of the preform should be initially at least 20 mm larger than the resected part of the artery which can be determined during preoperative examination of the patient. Beginning from the distal anastomosis between the ends of the artery and autotransplant, i.e. vascular autoprosthesis, circular sutures of the "end-to-end" type are applied using noninjuring needles with 5/0 synthetic thread 7 (FIG. 8). After removal of the distal and proximal vascular forceps the autoprosthesis is checked for patency and tightness of vascular sutures then the wound is drained and sutured layerwise.

Let us consider the use of the autotransplant in the capacity of autobypass on an example of femoral-popliteal bypassing. After making the diagnosis, the patient is administered aorto-arteriography to determine the indications for operation, and the preform 1 (FIG. 1) is modelled from a magnetic metal alloy. The preform diameter shall correspond to the anatomy of the affected femoral-popliteal segment while its length, taking in account the motor activity of the affected segment shall be approximately twice that of the affected fragment. Under local anesthesia with a 0.25-% solution of novocaine, using the packer 2 (FIG. 2) the preform 1 is embedded through the point-like skin section and the formed tunnel into the subcutaneous fat of the patient, disposing it on the front abdominal wall. The patient resumes his normal activity for 21–29 days and is admitted to the hospital before operation. On the day of operation the patient is given anesthesia then the skin is opened by a linear section in the projection of the preform 1 (FIG. 3) at the point of its location, the preform 1 with the biocapsule 3 is exposed from the surrounding tissues, the edges of the capsule are cut off with a scalpel stepping back up to 10 mm (FIG. 4) from both ends, the preform (FIG. 5) is pulled out from the capsule and the resulting autotransplant is used as an autobypass for femoral-popliteal bypassing. At the same time a medial access 6 to the femoral-popliteal segment is prepared. The length of the affected fragment is determined on the basis of the examination data and corrected on the basis of vision intraoperative anatomic data. The length of the autotransplant is made to match the required length of the femoral-popliteal bypass (FIG. 9). The blood flow more proximal to and more distal from the affected fragment within the limits of the intact portions of the artery is stopped by application of vascular forceps. Preparation of the distal and proximal ends of the grown autotransplant corresponds fully to preparation of the autovein in the traditional operation. The ends of the autotransplant are cut off at an angle of 45 deg (FIG. 10), then the incision is extended to match the diameter of the artery being bypassed (FIG. 11). Then the "end-to-side" distal anastomosis with the sound portion of the popliteal artery is applied by a standard method and a proximal anastomosis with the femoral artery (FIG. 12) is applied by the similar method. Preliminarily, the bypass is applied subcutaneously in the tunnel of the popliteal fossa. The anastomoses of the "end-to-side" are applied by means of noninjuring needles with a synthetic suturing material 8 using 6/0 thread. After the blood flow has been restarted, checks are made of the autobypass and artery downstream the distal anastomosis for pulsation. Finally, the wound is drained and sutured layerwise.

Let us consider the use of an autotransplant for an autopatch exemplified by an indirect "patch" isthmoplasty during coarctation of aorta. After making a diagnosis, the patient is administered aortography to determine indications for operation, then a preform 1 is modelled from a magnetic metal alloy. The length and diameter of the preform shall correspond to the anatomy of the affected fragment of the thoracic aorta. Under the local anesthesia with a 0.25% solution of novocaine and using a packer 2 the preform 1 is embedded through a point-like skin incision into a formed tunnel in the subcutaneous fat on the front abdominal wall of the patient. The latter resumes his normal activity at home for 21–29 days and is hospitalized before the operation. On the day of the operation the patient is administered surgical anesthesia to get access to the point of aorta coarctation through the left side thoracotomy in the 4th intercostal space. Simultaneously, the skin is dissected by a linear incision in the projection of the preform 1 and the latter is exposed together with the biocapsule 3 formed around it from the surrounding tissues.

Figure 13:
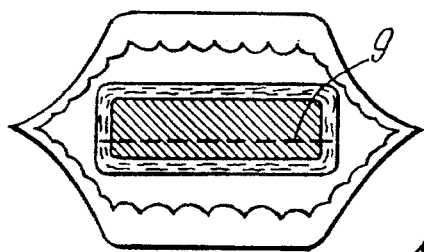
FIG. 13—dissection of autocapsule along preform during "patch" isthmoplasty of aorta.
Figure 14:
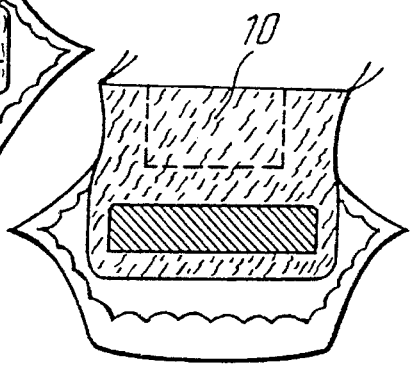
FIG. 14—cutting-out the autopatch, diagrammatic.

The biocapsule is prepared by dissecting it along the preform (FIG. 13), turning up the edges of the biocapsule by ligatures, and cutting out a "patch" from its wall (FIG. 14). The size of the "patch" is determined by preliminary examination and corrected on the basis of the visual intraoperative anatomic data.

Figure 15:
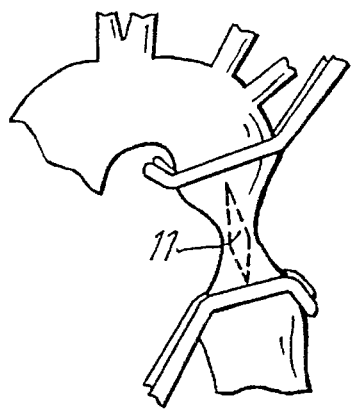
FIG. 15—longitudinal dissection of the front wall of aorta during its coarctation, diagrammatic.
Figure 16:
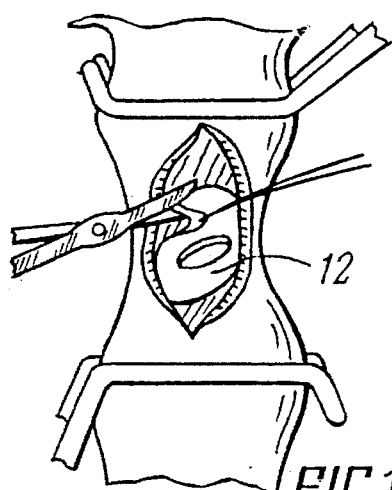
FIG. 16—excision of diaphragm during coarctation of aorta, diagrammatic.

Using an aorta coarctation clamp, the aorta is squeezed proximally to, and distally from, the point of coarctation. The stenotic portion of the aorta is opened by a longitudinal incision of its front surface (FIG. 15). The diaphragm is excised in the aorta lumen (FIG. 16) and the autopatch 13 (FIG. 18) cut out from the biocapsule to fit the dimensions of the defect is sutured into said lumen using a blanket suture. Then the vascular clamps are removed, beginning from the distal one. After the blood flow has been restarted the pulsation of the aorta is checked distally from the applied autopatch and the wound is sutured up layerwise.

Let us consider the use of autotransplant as an aortocoronary bypass.

Upon making a diagnosis the patient suffering from ischemia is administered coronarography to determine the occluded portions of the coronary arteries and establish the indications for the surgical intervention.

Relying on the data of coronarography the preform 1 (FIG. 1) is modelled from a magnetic metal alloy. The number, length and diameter of the preforms shall correspond to the anatomy of the damaged coronary arteries.

Under local anesthesia with a 0.25-% solution of novocaine and using the packer 2 (FIG. 2) the preform 1 is implanted into the patient's subcutaneous fat on the front abdominal wall through the point-like skin incision.

If it is planned to make a plurality of aorto-coronary bypasss, the preforms are disposed in the subcutaneous fat of the front abdominal wall, left and right of the median line at a distance not less than 60 mm from one another.

The patient resumes his normal activity for 21–29 days then is hospitalized before the operation. On the day of operation, the patient is given anesthesia, the coronary arteries are made accessible through median sternotomy and a linear incision is made in the projection of the preform to dissect the skin at the location of the preform 1 (FIG. 3), the latter together with the capsule 3 formed around it from the surrounding tissues is exposed, the edges of the capsule are ablated with a scalpel stepping back up to 1 cm from its both ends (FIG. 4), the preform 1 (FIG. 5) is pulled out of the capsule and the resulting autotransplant (FIG. 6) is used as an autobypass for aorto-coronary bypassing. The operating of aorto-coronary bypassing is carried by standard methods without taking the autovenous transplant from the lower extremity (large subcutaneous vein). Then the ascending part of the aorta and caval veins are cannulated, an artificial blood circulation apparatus is connected and the ascending part of the aorta is clamped with cardioplegic heart arrest.

Preparation of the distal and proximal ends of the grown autotransplant corresponds fully to the preparation of the autovein in the traditional operation: the ends of the autotransplant are cut at an angle of 45 deg (FIG. 10), the incision is extended in accordance with the diameter of the coronary artery (FIG. 11), the transplant is overturned through 180 deg and a distal "end-to-side" anastomosis with the coronary artery is applied by a blanket suture with a noninjuring needle and a 6/0 synthetic thread. Then the forceps are removed from the ascending aorta and the cardiac activity is restored.

The proximal anastomosis of the "end-to-side" type with the aorta is applied on the parietally forced-off aorta by the similar methods (FIGS. 10 and 11) using noninjuring needles and synthetic thread 5/0. After application of the aorto-coronary bypass (FIG. 18) and checking its patency the artificial circulation apparatus is disconnected, the cannulas are removed, the stermotomic incision is sutured up and the pericardium cavity is drained.

The method was realized on 9 patients and is illustrated by the examples below.

EXAMPLE 1

Figure 4:
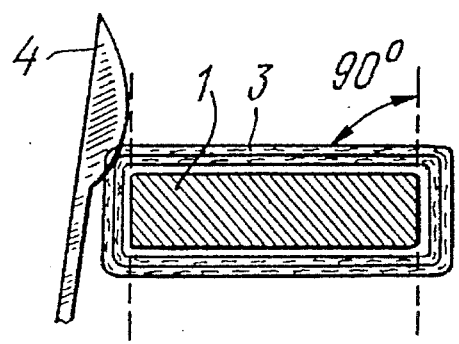
FIG. 4 shows cutting off with a scalpel the edges of the biocapsule formed around the preform.
Figure 5:
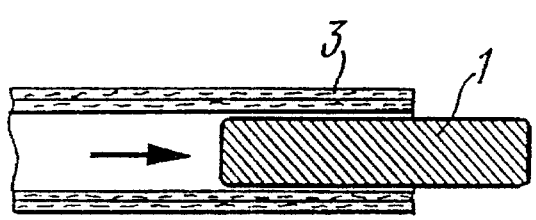
FIG. 5—removal of the preform from the biocapsule, diagrammatic.
Figure 6:
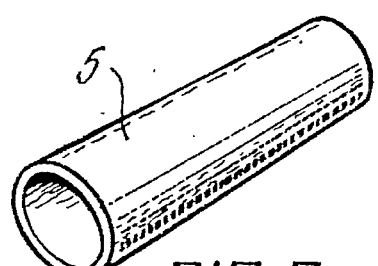
FIG. 6 shows the autotransplant after removal of the preform.

Patient S., 66, was admitted to the surgical clinic of the Khabarovsk Medical Institute complaining of quick fatiguability while walking, severe pains in the dextral shin and foot under moderate physical strain and at rest, edemic condition of the lower dextral extremity, aggravating after walking. Fell ill in 1985. Examination in April 1991 has registered a drop of temperature of the skin in the middle third of the dextral shin and foot, weak pulsation on the dextral popliteal artery and its absence on the back side of the foot, edemic condition of soft tissues. Aortography revealed occlusion of the dextral femoral artery on a length of 5 cm with satisfactory filling of the popliteal segment, stenosis up to 50% of the sinistraliliac artery. On Apr. 26, 1991 under local anesthesia with novocaine a point-like incision of skin was made in the projection of the midclavicular line, dextrally on the front abdominal wall. A preform 9 cm long, 8 mm in diameter of cobalt-samarium alloy was placed into a tunnel made by a straight packer in the subcutaneous fat. The wound was stitched up with two interrupted sutures. A second operation was made on expiration of 25 days, on May 22, 1991. Access was made to impassable portion pf the dextral femoral artery (through median incision (FIG. 7)) The preform together with the biological capsule formed around it (FIG. 3) the preform was exposed through the skin incision made in the preform projection. The capsule edges were cut off by stepping back 1 cm from each edge, and the preform of a permanent magnet was pulled out from the biocapsule (FIGS. 4, 5). Now the biocapsule took the form of a vascular prosthesis (FIG. 6). After application of two vascular clamps, the occluded portion of the dextral femoral artery was ablated on a length of 7 cm. Circular Carrel's sutures of the "end-to-end" type were put between the ends of the artery and autotransplant (FIG. 8) and the wound was stitched up layerwise. After 26 days the patient was discharged in a satisfactory condition for future observation by a vascular surgeon. Eight months after the operation a control examination showed that pulsation of the shin artery and popliteal artery on the dextral side was distinct. A control aortography evidenced a complete competence of the autotransplant. There were no complaints of pains while walking and no edemas. The patient resumed his normal activity.

EXAMPLE 2

Patient V., 52, was admitted to the surgical clinic of the Khabarovsk Medical Institute complaining of pains in gastrocnemic muscles, mostly on the sinistral side, intermittent lameness after a 100-m walk, as well as pains at rest, not yielding to conservative therapy. Symptoms began in 1986. An examination in October 1991 revealed a drop of skin temperature on both shins and feet, atrophy of skin, subcutaneous fat and muscles of shin as well as hyperkeratosis with fissures painful for palpation, callosity of plantar surface of the foot, more sinistrally. Pulsation of the sinistral popliteal artery is not felt and is weak on the back surface of the foot. Pulsation of the sinistral femoral arteries and that of the arteries in the dextral lower extremity is normal. A translumenal aorto-arteriography revealed a sementary occlusion of the proximal part of the sinistral popliteal artery on a length of 4 cm without defects of its bifurcation and with satisfactory filling of the distal and proximal bed. Examination of the dextral side revealed hemodynamically negligible (up to 40%) stenoses of the surface femoral artery. These data were confirmed by ultrasonic dopplerography as well as by thermometry, rheovasography and volumetric sphygmography. On Oct. 23, 1991 a point-like incision of skin was made dextrally on the front abdominal wall under local anesthesia with a 0.25-% novocaine solution. A tunnel in the subcutaneous fat was made with a straight packer and a preform 110 mm long, and 6 mm dia of the permanent magnet (FIG. 1) made from a cobalt-samarium alloy was inserted thereinto. The wound was stitched up by two interrupted sutures (FIG. 2). On expiration of 26 days, on Nov. 19, 1991 a second operation was made. A medial access was provided to the occluded portion of the sinistral popliteal artery (FIG. 9) and the biological capsule together with the preform was exposed through a skin incision in the projection of said preform. The biocapsule edges were resected by stepping back 10 mm from each edge and the preform was pulled out from the permanent magnet (FIGS. 4, 5). The biocapsule acquired the shape of a vascular autobypass (FIG. 6). According to the standard methods, the first step was to apply a distal anastomosis with the affected portion of the artery, then a proximal anastomosis with the femoral artery was made. This was preceded by driving the autobypass subcutaneously in the tunnel of the popliteal fossa. After the resumption of the blood flow, the pulse became distinct on the autobypass and on the artery downstream of the distal anastomosis. The anastomoses of the "end-to-side" type were applied with noninjuring needles, using a synthetic thread 6/0 and an ×4 optical magnification. Then the wound was drained and stitched up layerwise. After 11 days, the patient was discharged from the hospital for observation by a vascular surgeon. A control examination after 7 months revealed a distinct pulsation in the sinistral popliteal fossa and in the shin and foot arteries. Control aorto-arteriography shown a complete competence of the autotransplant. No complaints of pains while walking and at rest. The patient resumed his normal routine of life.

EXAMPLE 3

Patient A., 21, was admitted to the surgical clinic of the Khabarovsk Medical Institute complaining about headaches, dizziness, nasal bleeding, quick fatiguability, pains in the cardiac region, weakness in lower extremities, pains in gastrocnemic muscles while walking. Congenital illness. Condition deteriorated from 1989. An examination in November of 1991 revealed. Intensified pulsation of carotid arteries and aortic arch in the jugular fossa. Pulsation in the arteries of upper proximities is very tense and full and is absent on the femoral arteries. The arterial pressure on the upper and lower proximities, 160/90 and 120/0 mm Hg, respectively. Auscultation of the heart shown an intensive systolic murmur in the second sinistral intercostal space, systolic murmur in the neck vessels and in the sinistral interscapular space. The X-ray roentgenogram shown enlargement of the heart at the left ventricle, the contrasting esophagus is inclined to the left at the point of aorta constriction. Extasia of the ascending aorta and left subclavian artery. The ECG showed signs of hypertrophy of the left ventricle and a relative coronary insufficiency in the form of changes in the end portion of the ventricular complex. The echocardiography findings revealed an isolated "adult" version of aorta coarctation (stenosis downstream of ligamentum orteriosum).

Aortography showed dilatation of the ascending part of the aorta, brachycephalic vessels and subclavian artery. Downstream of the branching-off sinistral subclavian artery a partial stenosis of the thoracic aorta reached ½ of its diameter on a length of 30 mm. A sinistral ventriculography showed no defects in the contractile function of the myocardium. The end diastolic pressure of the left ventricle, 15 mm Hg.

Figure 17:
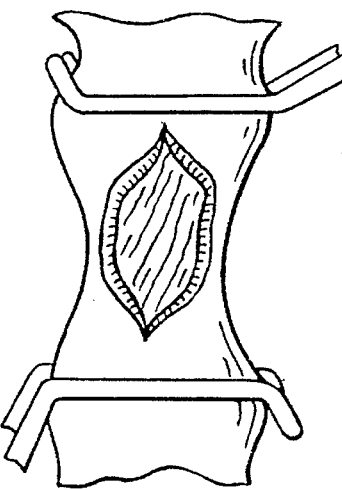
FIG. 17—aorta cavity after excision of diaphragm.

On Nov. 21, 1991, a point-like incision of skin was made on the sinistral front abdominal wall under local anesthesia with a 0.25-% novocaine solution. A tunnel was made with a straight packer in the subcutaneous fat and a preform of cobalt-samarium alloy 50 mm long of 20 mm dia (FIGS. 1, 2) was inserted thereinto. The wound was stitched up with two interrupted sutures. After 26 days, on Dec. 18, 1991 a second operation included providing access to the point of aorta coarctation through a sinistral side thoracotomy in the 4th intercoastal space. Simultaneously, the preform complete with the surrounding biological capsule (FIG. 8) was exposed through a skin incision. The biocapsule was dissected along the preform (FIG. 13). The edges of the biocapsule were bent up on the ligatures and a 30 mm×25 mm "patch" (FIG. 14) was cut out from the biocapsule wall. The aorta was clamped with two forceps and dissected by a longitudinal incision along its front surface to the mouth of the sinistral subclavian artery (FIG. 15). The diaphragm in the aorta lumen was dissected (FIG. 16) and the autopatch from the biocapsule (FIG. 18) corresponding to the size of the defect was stitched with a blanket suture into the diastasis of the incision (FIG. 17). After remedying the defect the wound was stitched up layerwise. In the period immediately following the operation the patient felt considerably better: headaches and pains in the gastrocnemic muscles vanished. The arterial pressure was normalized to 130/80 mm Hg on the upper and lower extremities. On the 12th day the patient was discharged in satisfactory condition under the observation of a vascular surgeon. After 7 months a control aortography showed complete restoration of the lumen in the thoracic aorta and full competency of the autopatch. No complaints. The patient resumed his normal activity.

I claim:

1. A method for surgical correction of vascular occlusions comprising:

determining the affected portion of the vessel;

modelling and making a magnetic alloy preform corresponding in shape and size to said affected portion of the vessel;

embedding said preform into the subcutaneous fat of the patient for 21–29 days until it becomes overgrown with a 3-layer biological capsule;

exposing said biological capsule from the surrounding tissues;

removing said preform from said biological capsule to produce an autotransplant;

cutting out a fragment from said autotransplant, corresponding in shape and size to said affected portion of the vessel;

resecting said affected portion of the vessel;

stitching up said cut-out fragment of the autotransplant in place of the resected portion of the vessel.

2. A method for surgical correction of vascular occlusions comprising:

determining the affected portion of the vessel;

modelling and making a magnetic alloy preform corresponding in shape and size to said affected portion of the vessel;

embedding said preform into the subcutaneous fat of the patient for 21–29 days until it becomes overgrown with a 3-layer biological capsule;

exposing said biological capsule from the surrounding tissues;

removing said preform from said biological capsule to produce an autotransplant;

cutting out a fragment from said autotransplant, corresponding in shape and size to said affected portion of the vessel;

stitching said cut-out fragment of the autotransplant into said affected vessel in the form of a bypass around said affected portion of the vessel.

* * * * *

UNITED STATES PATENT AND TRADEMARK OFFICE
CERTIFICATE OF CORRECTION

Figure 18:
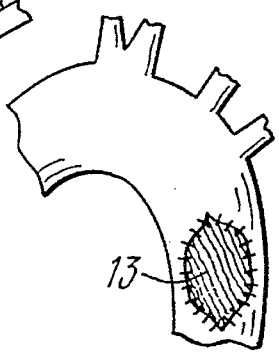
FIG. 18—operation involving indirect isthmoplasty with "patch" cut from autotransplant, diagrammatic.
Figure 19:
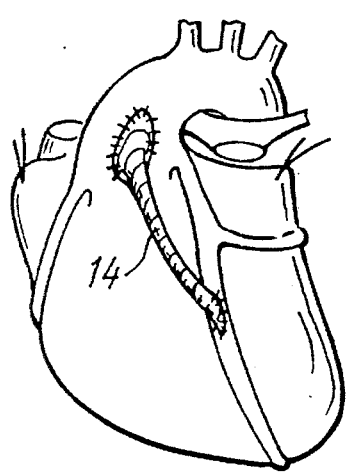
FIG. 19—using autotransplant as autobypass during aorto-coronary shunting.

PATENT NO. : 5,472,404
DATED : December 5, 1995
INVENTOR(S) : Valentin E. VOLGUSHEV It is certified that error appears in the above-indentified patent and that said Letters Patent is hereby corrected as shown below:

Column 7, line 43    change "Fig. 18" to -- Fig. 19 --.

Column 9, line 63    change "Fig. 8" to -- Fig. 3 --.

Signed and Sealed this

Second Day of April, 1996

Attest:

BRUCE LEHMAN

Attesting Officer    Commissioner of Patents and Trademarks